United States Patent [19]

Pütter et al.

[11] 4,341,719

[45] Jul. 27, 1982

[54] PROCESS FOR THE PREPARATION OF 1-AMINO-2-ETHOXY-NAPHTHALENE-6-SULPHONIC ACID

[75] Inventors: Rolf Pütter, Duesseldorf; Theodor Pfister, Wuppertal; Manfred Niese, Leverkusen; Peter Wenzl, Cologne, all of Fed. Rep. of Germany

[73] Assignee: Bayer Aktiengesellschaft, Leverkusen, Fed. Rep. of Germany

[21] Appl. No.: 238,327

[22] Filed: Feb. 26, 1981

[30] Foreign Application Priority Data

Mar. 18, 1980 [DE] Fed. Rep. of Germany ....... 3010372

[51] Int. Cl.³ ............................................. C07C 143/66
[52] U.S. Cl. .................................................... 260/509
[58] Field of Search ......................................... 260/509

[56] References Cited

U.S. PATENT DOCUMENTS 4,260,558  4/1981  Pfister ................................. 260/509

*Primary Examiner*—Nicky Chan
*Attorney, Agent, or Firm*—Sprung, Horn, Kramer & Woods

[57] ABSTRACT

A process for the preparation of 1-amino-2-ethoxy-naphthalene-6-sulphonic acid from 2-hydroxy-naphthalene-6-sulphonic acid which comprises:

A. contacting 2-hydroxy-naphthalene-6-sulphonic acid with at least an equimolar amount of an alkali metal nitrite in aqueous solution or suspension in the presence of hydrochloric acid, solution or suspension having a pH in the range of 2 to 5 and being at a temperature of 0° to 20° C.;

B. reducing the reaction product of step A in an aqueous suspension by contacting the same with excess iron in the presence of at least an equivalent amount of iron-II ions, relative to the reaction product obtained according to step A, in the presence of a mineral acid at a temperature from 50° to 120° C., and treating the thus-obtained reaction mixture with aqueous alkali metal hydroxide in the presence of iron oxide;

C. contacting the product of step B with excess acetic anhydride in an aqueous solution or suspension at a pH in the range of 3 to 10 at a temperature from 0° to 100° C.;

D. contacting the product of step C with an ethylating agent in the presence of an acid binding agent in an aqueous-organic solvent or diluent in a pH range from 8 to 14 at a temperature from 20° to 150° C.; and E. deacetylating the product of step D by contacting the same at reflux with an aqueous alkali metal hydroxide.

12 Claims, No Drawings

PROCESS FOR THE PREPARATION OF 1-AMINO-2-ETHOXY-NAPHTHALENE-6-SULPHONIC ACID

The invention relates to a process for the preparation of 1-amino-2-ethoxy-naphthalene-6-sulfphonic acid from 2-hydroxy-naphthalene-6-sulphonic acid.

It is known (German Democratic Republic Pat. No. 9,728) that ethers of amino-hydroxy compounds of dinuclear hydrocarbons and their nuclear-substituted derivatives, for example sulphonic acids, can be prepared by converting the amino-hydroxy compounds or their derivatives into the N-acyl compounds with acid anhydrides or acid chlorides in aqueous solution, etherifying the N-acyl compounds in a known manner and subsequently splitting off the acyl group by saponification.

According to Examples 2 and 3 of German Democratic Republic Pat. No. 9,728, 1-amino-2-ethoxy-naphthalene-6-sulphonic acid, is obtained by a procedure in which, in a first stage, 1-acetamino-2-hydroxy-naphthalene-6-sulphonic acid is prepared from 1-amino-2-hydroxy-naphthalene-6-sulphonic acid by reaction with acetic anhydride in dilute acetic acid, this intermediate product is etherified, in a second stage, with diethyl sulphate or with ethyl chloride in aqueous-alcoholic sodium hydroxide solution to give 1-acetamino-2-ethoxy-naphthalene-6-sulphonic acid, and, finally, this intermediate product is deacetylated, without intermediate isolation, by heating with aqueous sodium hydroxide solution to give 1-amino-2-ethoxy-naphthalene-6-sulphonic acid.

The yield of 1-amino-2-ethoxy-naphthalene-6-sulphonic acid is only about 67%, relative to the 1-amino-2-hydroxy-naphthalene-6-sulphonic acid employed. The process described in German Democratic Republic Pat. No. 9,728 is thus unsuitable for large-scale industrial production.

A process has now been found for the preparation of 1-amino-2-ethoxy-naphthalene-6-sulphonic acid from 2-hydroxy-naphthalene-6-sulphonic acid, which is characterised in that (a) 2-hydroxy-naphthalene-6-sulphonic acid and at least the equimolar amount of an alkali metal nitrite are initially introduced into the reaction vessel in aqueous solution or suspension and are reacted, with the addition of hydrochloric acid, in a pH range from 2 to 5 and at temperatures from 0° to 20° C. (b) the reaction product obtained, if necessary after salting out, is reduced in aqueous suspension with excess iron in the presence of at least an equivalent amount of iron-II ions, relative to the reaction product obtained according to step (a), and in the presence of mineral acid at temperatures from 50° to 120° C., and the reaction mixture is then treated with aqueous alkali metal hydroxide in the presence of iron oxide and, if appropriate, in the presence of a reducing compound at temperatures from 80° to 110° C., (c) the product obtained according to step (b) is reacted with excess acetic anhydride in aqueous solution or suspension, if appropriate after adding mineral acid, in a pH range from 3 to 10 and at temperatures from 0° to 100° C., and (d) the product obtained, if necessary after salting out, is reacted with an ethylating agent in the presence of acid-binding agents and in an aqueous-organic solvent or diluent, if appropriate in the presence of potassium compounds, in a pH range from 8 to 14 and at temperatures from 20° to 150° C., and the reaction product is then deacetylated at the reflux temperature with aqueous alkali metal hydroxide.

The process according to the invention can be represented, for example, by the following equation:

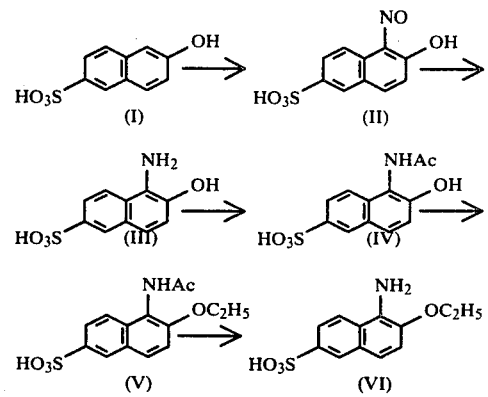

The formulae (I) to (VI) in each case show the free acids. However, they also represent alkali metal salts or alkaline earth metal salts thereof, in particular the sodium and potassium salts, and mixtures of the acids with their salts and mixtures of the salts with one another.

In general, the process according to the invention is carried out as follows:

Hydrochloric acid is metered into an aqueous solution or suspension of 2-hydroxy-naphthalene-6-sulphonic acid (I) and an alkali metal nitrite, such as lithium nitrite, sodium nitrite, potassium nitrite and/or rubidium nitrite, preferably sodium nitrite, at temperatures from 0° to 20° C., preferably 5° to 15° C., in a manner such that a pH value in the range from 2 to 5, preferably 3 to 4.5, is established in the reaction mixture.

In the process according to the invention, the alkali metal nitrite is employed in at least the equimolar amount, relative to the 2-hydroxy-naphthalene-6-sulphonic acid. 1.00 to 1.2 mols of alkali metal nitrite per 1 mol of 2-hydroxy-naphthalene-6-sulphonic acid are preferably employed.

The hydrochloric acid can be added to the reaction mixture either in aqueous form or in concentrated form. For example, the hydrochloric acid can be added as 10 to 40% strength by weight hydrochloric acid, preferably as 25 to 35% strength by weight hydrochloric acid.

The nitrosation product (II), which, if necessary, has been salted out, by adding, for example, sodium chloride, after stirring the mixture for several hours (about 1 to 5 hours) or after leaving the mixture to stand overnight, is then reacted with excess iron, preferably 10 to 30 mols of iron per 1 mol of nitrosation product, in the presence of at least an equivalent amount of iron-II ions, relative to the nitrosation product, and in the presence of mineral acid, such as hydrochloric acid and/or sulphuric acid, preferably hydrochloric acid, in aqueous suspension at temperatures from 50° to 120° C., preferably at 80° to 110° C.

For the process according to the invention, it is important that at least an amount of iron-II ions equivalent to the amount of nitrosation product is present in dissolved form in the aqueous suspension at the start of the reaction.

As iron-II ions in the process according to the invention, there may be employed: iron-II chloride and/or iron-II sulphate, preferably iron-II chloride. 0.5 to 1.5 mols of iron-II ions are preferably introduced per mol of nitrosation product.

A procedure is followed in which an appropriate amount of an iron-II salt is dissolved in the aqueous suspension, or this salt is produced in situ by using an appropriate acid.

After the reduction, the reaction mixture is treated with aqueous alkali metal hydroxide, such as lithium hydroxide, sodium hydroxide, potassium hydroxide and/or rubidium hydroxide, preferably sodium hydroxide, in the presence of iron oxide, such as iron-II/III oxide, and if appropriate in the presence of a reducing compound, such as sodium sulphite, sodium dithionite or Rongalit ®, preferably sodium sulphite, at temperatures from 80° to 110° C., preferably 85° to 100° C. The purpose of this step is to dissociate the complex compound of 1-amino-2-hydroxy-naphthalene-6-sulfonic acid with iron and to crystalyse the bonded iron for better filtration (see Example 4).

The amount of iron oxide to be added is not critical. In general, 0.01 to 0.5 mol, preferably 0.1 to 0.3 mol, of iron oxide, relative to the 1-nitroso-2-hydroxy-naphthalene-6-sulphonic acid (II) employed, is added to the reaction mixture.

The amount of reducing compounds which may be added to the reaction mixture can also vary within wide limits. 0.005 to 0.1 mol, preferably 0.01 to 0.05 mol, of reducing substance, relative to the nitrosation product (II) employed, is usually added.

The hydrochloric acid employed for the reduction can be added to the reaction mixture either in aqueous form or in concentrated form. It is expedient to add the hydrochloric acid in concentrated form. The amount of hydrochloric acid can vary within wide limits. In general, 0.1 to 5.0 mols, preferably 0.5 to 3.0 mols, of hydrochloric acid per mol of 1-nitroso-2-hydroxy-naphthalene-6-sulphonic acid are added for the reduction.

The amount of aqueous alkali metal hydroxide employed for the dissociation of the complex compound of 1-amino-2-hydroxy-naphthalene-6-sulfonic acid with iron is likewise not critical. 1.0 to 5.0 mols, preferably 1.5 to 3.0 mols, of aqueous alkali metal hydroxide per mol of 1-nitroso-2-hydroxynaphthalene-6-sulphonic acid are usually added to the reaction mixture.

For acetylation of the resulting 1-amino-2-hydroxy-naphthalene-6-sulphonic acid (III), after the iron compounds obtained during the treatment of the reduction mixture with iron oxide have been separated off, for example by filtration, the aqueous solution or suspension of the amino compound (III) is, if necessary, brought to a pH value of 3 to 10, preferably 5 to 8, by adding mineral acid, such as hydrochloric acid, and is reacted with excess acetic anhydride, preferably 1.05 to 1.3 mols per mol of amino compound (III), at temperatures from 0° to 100° C., preferably at 20° to 60° C.

In a preferred embodiment, the iron required for the reduction is initially introduced into water, together with the iron-II salts, and this suspension is heated to the abovementioned reaction temperature (50° to 120° C.), during which concentrated hydrochloric acid is added dropwise. The nitrosation product is then introduced in portions into the iron/iron-II salt/water mixture. Sodium sulphite and iron oxide are then added to the reaction mixture and nitrogen is passed over the mixture. The reaction mixture is subsequently treated with sodium hydroxide solution at 80° to 100° C. and the iron compounds which have precipitated are filtered off.

The 1-amino-2-hydroxy-naphthalene-6-sulphonic acid (III) is then acetylated in the manner described above.

The 1-acetamino-2-hydroxy-naphthalene-6-sulphonic acid (IV) obtained after the acetylation, if necessary after salting out with, for example, sodium chloride, is then reacted with an ethylating agent in the presence of an acid-binding agent in an aqueous-organic solvent or diluent, in a pH range from 8 to 14 and at temperatures from 20° to 150° C. In certain circumstances, it may be necessary to add further acid-binding agents during the reaction in order to maintain the pH range.

Ethylating agents which can be used are, for example: ethyl chloride, ethyl bromide, ethyl iodide, diethyl sulphate or triethyl phosphite, preferably ethyl chloride or diethyl sulphate.

The ethylating agents are in general employed in amounts of 1 to 5 mols, preferably 1.5 to 3 mols, per mol of 1-acetamino-2-hydroxy-naphthalene-6-sulphonic acid.

The bases customarily used in aqueous solution can be employed as the acid-binding agents. Possible bases are, in particular, alkali metal hydroxides, such as sodium hydroxide and/or potassium hydroxide, and alkali metal carbonates, such as sodium carbonate and/or potassium carbonate.

The acid-binding agents can be employed in amounts of 1 to 5 mols, preferably 1.2 to 3 mols, per mol of 1-acetamino-2-hydroxy-naphthalene-6-sulphonic acid.

Possible aqueous-organic solvents or diluents are mixtures of water and water-miscible organic solvents or diluents. These include, in particular, alcohols, such as methanol, ethanol and n- and isopropanol, ketones, such as acetone and methyl ethyl ketone, and cyclic ethers, such as tetrahydrofuran and dioxane.

The amount of aqueous-organic solvent or diluent added is in general 0.3 to 3:1, preferably 0.5 to 2:1, per mol of 1-acetamino-2-hydroxy-naphthalene-6-sulphonic acid.

In a preferred variant of the process according to the invention, diethyl sulphate is employed as the etherifying or ethylating agent. The etherification reaction is then carried out by a procedure in which 1-acetamino-2-hydroxy-naphthalene-6-sulphonic acid is initially introduced in a mixture of water and one of the abovementioned organic solvents or diluents (ratio of the mixture: 1:1 to 1:10, preferably 1:2 to 1:8) and the pH value is adjusted to 8 to 12, preferably 9 to 11, by adding base. It should be ensured that the pH value is kept in the given range throughout the reaction. Diethyl sulphate is then added dropwise in an amount of 1 to 3 mols, preferably 1.5 to 2.5 mols, per mol of 1-acetamino-2-hydroxy-naphthalene-6-sulphonic acid at a temperature from 30° to 90° C.

In another preferred variant of the process according to the invention, ethyl chloride is employed as the etherifying agent. This variant is carried out in an autoclave, preferably in the presence of potassium compounds, such as potassium hydroxide, potassium carbonate, potassium chloride and/or potassium acetate, preferably potassium hydroxide and/or potassium carbonate, using one of the abovementioned organic solvents or diluents, preferably methanol and/or ethanol, mixed with water. The potassium compounds are added in approximately the equimolar amounts, relative to 1-acetamino-2-hydroxy-naphthalene-6-sulphonic acid. 0.9 to 1.5 mols of potassium compound are preferably added per mol of 1-acetamino-2-hydroxy-naphthalene-6-sulphonic acid.

The ethyl chloride is employed in an amount of 1 to 5 mols, preferably 1.5 to 3 mols, per mol of 1-acetamino-2-hydroxy-naphthalene-6-sulphonic acid.

During the reaction, it should again be ensured that the pH value of the reaction mixture does not fall below 8 until the reaction has ended. If necessary, further alkali metal hydroxide solution is added during the reaction.

The deacetylation of the etherified product can then be carried out, after distilling off the organic solvent or diluent, in a known manner, for example by heating the mixture to the reflux temperature with aqueous alkali metal hydroxide, such as sodium hydroxide and/or potassium hydroxide. The aqueous alkali metal hydroxide is in general employed in excess. For this purpose there are present 1.5 to 15 mols of alkali metal hydroxide per mol of compound to be deacetylated.

The crystalline product obtained after the deacetylation can be isolated by vacuum filtration; the content of 1-amino-2-ethoxy-naphthalene-6-sulphonic acid (VI) is determined, for example, by diazotisation.

It is exceptionally surprising that 1-amino-2-ethoxy-naphthalene-6-sulphonic acid is obtained in particularly good yields and purities in a multi-stage reaction starting from 2-hydroxy-naphthalene-6-sulphonic acid by the process according to the invention.

This is so surprising since, in the process of German Democratic Republic Pat. No. 9,728, yields of 1-amino-2-ethoxy-naphthalene-6-sulphonic acid which are below 70% are obtained, although this process already uses 1-amino-2-hydroxy-naphthalene-6-sulphonic acid as the starting material. This is particularly so since the process of this invention comprises two fewer process steps.

The 1-amino-2-ethoxy-naphthalene-6-sulphonic acid prepared according to the invention can be used for the preparation of azo dyestuffs (see U.S. 2,636,030).

The following examples are intended to illustrate the process according to the invention, but without restricting it to these examples.

EXAMPLE 1

284 g (78.9% pure=224 g of 100% pure=1.0 mol) of 2-hydroxy-naphthalene-6-sulphonic acid and 69.0 g (1.0 mol) of sodium nitrite are initially introduced into 2.6 l of water. 160 ml of hydrochloric acid (18% strength) are added dropwise to this mixture at a temperature of 10° C. in the course of 3 hours, whilst stirring, so that a pH value of 4 is established. 500 g of sodium chloride are added to the resulting suspension and the mixture is stirred for 2 hours. The product is then filtered off, washed with sodium chloride solution and dried.

455 g (51.7% pure=235 g of 100%=93% of theory) of 1-nitroso-2-hydroxy-naphthalene-6-sulphonic acid are obtained in the form of yellow crystals.

EXAMPLE 2

1,250 parts of the sodium salt of 2-hydroxy-naphthalene-6-sulphonic acid (62.7% pure=784 parts of 100% pure) in 6,800 parts of water are heated to 70° to 75° C. until a clear solution is formed. The solution is then cooled to 5° to 10° C. 1,065 parts of 25% strength sodium nitrite solution are added to the finely crystalline suspension formed. 410 parts of 30% strength hydrochloric acid are now allowed to run in at 10° C., whereupon a pH value of about 4 is established, and the mixture is subsequently stirred for one hour and the product is salted out by slowly adding 1,400 parts of sodium chloride. The mixture is then subsequently stirred for a further 2 hours. After filtering off the product and washing it with sodium chloride solution, 2,800 parts of water-moist 1-nitroso-2-hydroxy-naphthalene-6-sulphonic acid (29.6% pure=829 parts, 100% pure=94% of theory) are obtained.

EXAMPLE 3

203 g of the sodium salt of 2-hydroxy-naphthalene-6-sulphonic acid (55.4% pure=112.5 g of 100% pure =0.5 mol) are introduced into 500 ml of water, and 152 g of 25% strength sodium nitrite solution (0.55 mol) are added to this mixture. After cooling the mixture to about 5° to 10° C., 59.5 g of 30% strength hydrochloric acid are added in the course of one hour, a pH value in the range from 2 to 5 being obtained. The mixture is subsequently stirred for one hour, 100 g of sodium chloride are then added and, after a further hour, the product is filtered off. The solid is washed with 100 ml of sodium chloride solution and dried in vacuo.

217 g of 1-nitroso-2-hydroxy-naphthalene-6-sulphonic acid with a content of 56% (=121.5 g of 100% pure=96% of theory) are obtained.

EXAMPLE 4

400 g of iron and 500 ml of water are heated to 90° to 95° C. in a 2 l beaker, whilst stirring. 32 ml of concentrated hydrochloric acid (30% strength=11 g of 100% strength=0.302 mol) are added during the heating. 240 g (30% pure=73 g of 100% pure=0.2875 mol) of 1-nitroso-2-hydroxy-naphthalene-6-sulphonic acid, which has been prepared according to Example 2, are introduced into the iron/water mixture at 90° to 95° C. in the course of 1.5 to 2 hours. The compound is added in small portions. After each addition, the reaction mixture assumes a deep green coloration, which disappears again after a short time. The light-grey complex compound of 1-amino-2-hydroxy-naphthalene-6-sulphonic acid already precipitates shortly after the start of the addition of the nitroso compound. The next portion of nitroso compound is added when the green coloration has disappeared. After the introduction of the nitroso compound, the contents of the beaker are introduced into a 2 l three-necked flask and nitrogen is passed over the mixture. 5 g of sodium sulphite and 20 g of 70% pure iron-II/III oxide are added to the reaction mixture. Thereafter, 35 ml of 50% strength sodium hydroxide solution (27 g of 100% strength=0.676 mol) are allowed to run in at 95° to 100° C. in the course of 2 to 5 minutes. The complex is thereby dissociated and the iron bonded separates out as a black precipitate. It is filtered off, 90 ml of concentrated hydrochloric acid (31 g of 100% strength=0.85 mol) being initially introduced into the receiver. During the filtration, 1-amino-2-hydroxy-naphthalene-6-sulphonic acid immediately precipitates in the receiver in the form of coarse crystals.

To prepare 1-acetamino-2-hydroxy-naphthalene-6-sulphonic acid, the mixture of 1-amino-2-hydroxy-naphthalene-6-sulphonic acid and the mother liquor is adjusted to pH 8 by adding 28 ml of 50% strength sodium hydroxide solution (21 g of 100% strength=0.54 mol). 0.5 g of sodium dithionite are added to this mixture. 32 ml (34 g=0.333 mol) of acetic anhydride are then allowed to run in at a temperature of 40° C. in the course of 5 minutes, the mixture is subsequently stirred for 5 minutes and the product is salted out by adding 240 g of sodium chloride. After stirring the mixture at 20° C. for several hours, the product is filtered off, washed with saturated sodium chloride solution and dried. 110 g of 1-acetamino-2-hydroxy-naphthalene-6-sulphonic acid are obtained in the form of almost colourless crystals (60.4% pure=66.3 g, 100% pure=0.236 mol).

This corresponds to a yield of 82% of theory, relative to 1-nitroso-2-hydroxynaphthalene-6-sulphonic acid, or 77% of theory, relative to 2-hydroxy-naphthalene-6-sulphonic acid.

EXAMPLE 5

400 g of iron, 500 ml of water, 42 g of iron-II sulphate. 7 $H_2O$ (0.151 mol) or 27 g of iron-III chloride. 6 $H_2O$ (0.1 mol) and 3 ml of concentrated hydrochloric acid are mixed with one another in a 2 l beaker and the mixture is heated to 95° to 100° C.

240 g (30% pure=73 g of 100% pure=0.2875 mol) of 1-nitroso-2-hydroxy-naphthalene-6-sulphonic acid, which have been prepared according to Example 2, are introduced into this mixture in the course of 1.5 to 2 hours.

The reaction mixture is subjected to further treatment in accordance with Example 4.

110 g of 1-acetamino-2-hydroxy-naphthalene-6-sulphonic acid (60.4% pure=66.3 g of 100% pure=0.236 mol) are obtained. This corresponds to a yield of 82% of theory, relative to 1-nitroso-2-hydroxynaphthalene-6-sulphonic acid, or 77% of theory, relative to 2-hydroxynaphthalene-6-sulphonic acid.

EXAMPLE 6

60.8 g (92.6% pure=56.3 g of 100% pure=0.2 mol) of purified (recrystallised) 1-acetamino-2-hydroxy-naphthalene-6-sulphonic acid, which have been prepared according to Example 4, are suspended in a mixture of 240 ml of ethanol and 40 ml of water. The pH value is adjusted to 9.5 by dropwise addition of 2 N sodium hydroxide solution. 46 ml (0.36 mol) of diethyl sulphate are added dropwise at a temperature of 40° to 50° C. in the course of 20 minutes, the pH value being kept at 9.5 to 10.5 by adding sodium hydroxide solution. The reaction mixture is stirred at the above-mentioned temperature for a further 3 hours, whilst maintaining the pH value. The alcohol is then distilled off and, after adding 44 ml of 50% strength sodium hydroxide solution, the mixture is heated under reflux for 2 hours. After cooling the mixture, the product which has precipitated is filtered off, washed with saturated sodium chloride solution and dried in vacuo.

61.7 g (72.0% pure=44.4 g of 100% pure=83% of theory) of 1-amino-2-ethoxy-naphthalene-6-sulphonic acid are obtained in the form of whitish-grey crystals.

EXAMPLE 7

60.8 g (92.6% pure=56.3 g of 100% pure=0.2 mol) of purified (recrystallised) 1-acetamino-2-hydroxy-naphthalene-6-sulphonic acid, prepared according to Example 4, are etherified analogously to Example 6, but with the difference that the pH value is obtained in the range from 9.0 to 10.0 and the reaction temperature is approximately 80° C. (reflux temperature of the solvent). The after-stirring time is thus shortened to about 30 minutes. The deacetylation is carried out as described in Example 6.

Yield: 50.8 g (78.6% pure=45.6 g of 100% pure=85% of theory) of 1-amino-2-ethoxy-naphthalene-6-sulphonic acid.

EXAMPLE 8

15.3 g (91.8% pure=14.0 g of 100% pure=0.05 mol) of purified (recrystallised) 1-acetamino-2-hydroxy-naphthalene-6-sulphonic acid, prepared according to Example 4, in 67 ml of methanol are warmed to 45° C. After the pH value has been adjusted to 10 with 2 N sodium hydroxide solution, 13.7 g (0.09 mol) of diethyl sulphate are added dropwise at a temperature of 40° to 50° C. in the course of 30 minutes. The mixture is subsequently stirred for a further 2 hours at 45° C., the pH value being kept at 10. The deacetylation is carried out as described in Example 6.

Yield: 13.1 g (83.2%=10.9 g of 100% pure=81.5% of theory) of 1-amino-2-ethoxy-naphthalene-6-sulphonic acid.

EXAMPLE 9

15.3 g (91.8% pure=14.0 g of 100% pure=0.05 mol) of purified (recrystallised) 1-acetamino-2-hydroxy-naphthalene-6-sulphonic acid, prepared according to Example 4, in a mixture of 60 ml of acetone and 10 ml of water are warmed to 45° C. The pH value is adjusted to 9 with sodium hydroxide solution. 13.7 g (0.09 mol) of diethyl sulphate are then added dropwise in the course of 10 minutes. The pH value is kept at 9.5 for a further 4 hours by adding sodium hydroxide solution. The deacetylation is carried out as described in Example 6.

Yield: 12.9 g (83.6% pure=10.8 g of 100% pure=81% of theory) of 1-amino-2-ethoxy-naphthalene-6-sulphonic acid.

EXAMPLE 10

15.3 g (91.4% pure=14.0 g of 100% pure=0.05 mol) of 1-acetamino-2-hydroxy-naphthalene-6-sulphonic acid, prepared according to Example 4, in a mixture of 67 ml alcohol and 12 ml of water are warmed to 45° C. The pH value is adjusted to 10 with 2 N sodium hydroxide solution. 13.7 g (0.09 mol) of diethyl sulphate are then added dropwise in the course of 20 minutes and the pH value is kept at 10 for a further 4 hours by adding sodium hydroxide solution. The alcohol is distilled off and, after adding 40 ml of 18% strength hydrochloric acid, the mixture is heated to boiling point under reflux for 2 hours. Working up is carried out as described in Example 6.

Yield: 16.2 g (70.8% pure=11.5 g of 100% pure=85% of theory) of 1-amino-2-ethoxy-naphthalene-6-sulphonic acid. According to analysis by thin layer chromatography, the product is contaminated with about 3% of 1-amino-2-hydroxy-napthalene-6-sulphonic acid.

EXAMPLE 11

15.3 g (92.1% pure=14.0 g of 100% pure=0.05 mol) of purified (recrystallised) 1-acetamino-2-hydroxy-naphthalene-6-sulphonic acid, prepared according to Example 4, are mixed with 134 ml of a solution of 9.7 g (0.15 mol) of ethyl chloride in ethanol, 23 ml of 2 N potassium hydroxide solution, 3.5 g (0.025 mol) of potassium carbonate and 2.6 g (0.025 mol) of sodium carbonst in a 0.3 l autoclave at room temperature and this mixture is stirred intensively at 120° C. for 5 hours. The contents of the autoclave are then evaporated to dryness and the residue is heated under reflux with 37 ml of water and 10 ml of 50% strength sodium hydroxide solution for 2 hours. After cooling, the product is filtered off, washed with saturated sodium chloride solution and dried at 50° C. in vacuo. 14.15 g (82% pure=11.6 g of 100% pure=87% of theory) of 1-amino-2-ethoxy-naphthalene-6-sulphonic acid are obtained.

EXAMPLE 12

6.42 kg (62% pure=4 kg of 100% pure) of 1-acetamino-2-hydroxy-naphthalene-6-sulphonic acid, prepared according to Example 4, 0.98 kg of potassium carbonate and 0.75 kg of sodium carbonate are introduced into a 150 l autoclave. After flushing the autoclave with nitrogen, 22 kg (28 l) of ethanol are added to the mixture. The autoclave is closed and heated to 120° C., whilst stirring thoroughly. 7 kg (6.5 l) of 2 N potassium hydroxide solution and 2.75 kg (about 3 l) of ethyl chloride are now pumped into the autoclave in the course of 1 to 2 hours. The entire reaction mixture is stirred for a further 5 hours at 120° C. After cooling the reaction mixture to room temperature, the autoclave is let down and flushed twice with nitrogen. The contents of the autoclave are then introduced into a 250 ml V4A steel kettle. The autoclave is rinsed out with 5 kg of 80% pure ethanol and the rinsing solution is likewise introduced into the steel kettle. The mixture in the steel kettle is heated to the boiling point, about 20 kg of alcohol being distilled off. 13 kg of water are then allowed to run slowly into the boiling solution and the mixture is distilled until no further alcohol passes over. After adding 4.3 kg of 50% strength sodium hydroxide solution, the mixture is stirred at 100° C. for 4 hours. The mixture is then cooled to 20° C. and the product which has precipitated is filtered off and washed with 25 kg of sodium chloride solution. After drying, 3.6 kg of 1-amino-2-ethoxy-naphthalene-6-sulphonic acid (content: 84.2% pure, corresponding to 3.03 kg of 100% pure=80% of theory, relative to 1-acetamino-2-hydroxy-naphthalene-6-sulphonic acid, or 61.6% of theory, relative to 2-hydroxy-naphthalene-6-sulphonic acid) are obtained.

EXAMPLE 13

98.1 g of 1-acetamino-2-hydroxy-naphthalene-6-sulphonic acid (71.7% pure=50.4 g of 100% pure=0.25 mol), prepared according to Example 4, are introduced into a 1.3 l autoclave. 34.6 g (0.25 mol) of potassium carbonate suspended in 500 ml of ethanol are added thereto. After heating the mixture to 120° C., 115 ml of 2 N potassium hydroxide solution and 54 ml (74 g=0.75 mol) of ethyl chloride are simultaneously pumped in. The reaction mixture is allowed to cool somewhat, the salt residue is filtered off and, after adding 100 g of water, 460 g of ethanol (water-containing) are distilled off from the filtrate. 50 ml of 50% strength sodium hydroxide solution are added dropwise to the mixture at a temperature of 98° C. After 2 hours, the reaction mixture is cooled to room temperature and the product which has precipitated is filtered off and washed with 100 ml of saturated sodium chloride solution. After filtering off and drying, 76.1 g of 1-amino-2-ethoxy-naphthalene-6-sulphonic acid (78.3% pure=60.0 g of 100% pure=90% of theory, relative to 1-acetamino-2-hydroxy-naphthalene-6-sulphonic acid, or 69.4% of theory, relative to 2-hydroxy-naphthalene-6-sulphonic acid) are obtained.

EXAMPLE 14

The reaction is carried out analogously to Example 13, but, instead of ethanol, the same amount of methanol is employed. 87.5 g of 1-amino-2-ethoxy-naphthalene-6-sulphonic acid (70.6% pure=61.8 g of 100% pure=92.5% of theory, relative to 1-acetamino-2-hydroxy-naphthalene-6-sulphonic acid or 71.2% of theory, relative to 2-hydroxy-naphthalene-6-sulphonic acid) are obtained.

EXAMPLE 15

12.5 parts of 1-acetamino-2-hydroxy-naphthalene-6-sulphonic acid (67.5% pure=8.5 parts of 100% pure), prepared according to Example 4, and 4.2 parts of potassium carbonate are suspended in a mixture of 47.4 parts by weight of methanol and 9.0 parts by weight of water in an autoclave. After heating the autoclave, 6.2 parts of 25% strength potassium hydroxide solution and 5.8 parts of ethyl chloride are simultaneously metered in at 120° C. The reaction mixture is worked up analogously to Example 12. 87% of theory of 1-amino-2-ethoxy-naphthalene-6-sulphonic acid, relative to 1-acetamino-2-hydroxy-naphthalene-6-sulphonic acid, or 67.8% of theory, relative to 2-hydroxy-naphthalene-6-sulphonic acid, are obtained.

EXAMPLE 16

25 parts by weight of 1-acetamino-2-hydroxy-naphthalene-6-sulphonic acid (67.5% pure=17 parts of 100% pure), prepared according to Example 4, and 8.3 parts of potassium carbonate are suspended in a mixture of 48 parts by weight of methanol and 18 parts by weight of water in an autoclave. 12.4 parts of potassium hydroxide solution (25% strength) and 11.6 parts of ethyl chloride are added at 120° C. When the reaction has ended, the resulting solution is worked up according to Example 12. After drying the product, 23.6 parts by weight of 1-amino-2-ethoxy-naphthalene-6-sulphonic acid (55% pure=12.98 parts of 100% pure=81% of theory, relative to 1-acetamino-2-hydroxy-naphthalene-6-sulphonic acid, or 62.4% of theory, relative to 2-hydroxy-naphthalene-6-sulphonic acid) are obtained.

What is claimed is:

1. A process for the preparation of 1-amino-2-ethoxy-naphthalene-6-sulphonic acid from 2-hydroxy-naphthalene-6-sulphonic acid which comprises:

A. contacting 2-hydroxy-naphthalene-6-sulphonic acid with at least an equimolar amount of an alkali metal nitrite in an aqueous solution or suspension in the presence of hydrochloric acid, the solution or suspension having a pH in the range of 2 to 5 and being at a temperature of 0° to 20° C.;

B. reducing the reaction product of step A in an aqueous suspension by contacting the same with excess iron in the presence of at least an equivalent amount of iron (II) ions, relative to the reaction product obtained according to step A, in the presence of a mineral acid at a temperature from 50° to 120° C., and treating the thus-obtained reaction mixture with aqueous alkali metal hydroxide in the presence of iron oxide;

C. contacting the product of step B with excess acetic anhydride in an aqueous solution or suspension at a pH in the range of 3 to 10 at a temperature from 0° to 100° C.;

D. contacting the product of step C with an ethylating agent in the presence of an acid binding agent in an aqueous-organic solvent or diluent in a pH range from 8 to 14 at a temperature from 20° to 150° C.; and E. deacetylating the product of step D by contacting the same at reflux with an aqueous alkali metal hydroxide.

2. A process according to claim 1, wherein in step B the treatment with iron oxide is performed in the presence of a reducing compound.

3. A process according to claim 1, wherein in accordance with step C the treatment of the reaction product according to step B with excess acetic anhydride is effected after adding a mineral acid.

4. A process according to claim 1, wherein step D is effected in the presence of at least one potassium compound.

5. A process according to claim 1, wherein the reaction product from step A is salted out prior to the reduction of step B.

6. A process according to claim 1, wherein step B is performed without salting out the product of step A.

7. A process according to claim 1, wherein in step A 1.00 to 1.2 mols of alkali metal nitrite are employed per mol of 2-hydroxy-naphthalene-6-sulphonic acid.

8. A process according to claim 1, wherein in step B 10 to 30 mols of iron are employed per mol of 1-nitroso-2-hydroxy-naphthalene-6-sulphonic acid.

9. A process according to claim 1, wherein in step B 0.5 to 1.5 mols of iron (II) ions are employed per mol of 1-nitroso-2-hydroxy-naphthalene-6-sulphonic acid.

10. The process according to claim 1, wherein the ethylating agent employed in step D is employed in an amount of 1.5 mols per mol of 1-acetamido-2-hydroxy-naphthalene-6-sulphonic acid.

11. A process according to claim 1, wherein the ethylating agent is diethylsulphate or ethyl chloride.

12. A process for the preparation of 1-amino-2-ethoxy-naphthalene-6-sulphonic acid from 2-hydroxy-naphthalene-6-sulphonic acid which consists essentially of:

A. contacting 2-hydroxy-naphthalene-6-sulphonic acid with at least an equimolar amount of an alkali metal nitrite in an aqueous solution or suspension in the presence of hydrochloric acid, the solution or suspension having a pH in the range of 2 to 5 and being at a temperature of 0° to 20° C.;

B. reducing the reaction product of step A in an aqueous suspension by contacting the same with excess iron in the presence of at least an equivalent amount of iron (II) ions, relative to the reaction product obtained according to step A, in the presence of a mineral acid at a temperature from 50° to 120° C., and treating the thus-obtained reaction mixture with aqueous alkali metal hydroxide in the presence of iron oxide;

C. contacting the product of step B with excess acetic anhydride in an aqueous solution or suspension at a pH in the range of 3 to 10 at a temperature from 0° to 100° C.

D. contacting the product of step C with an ethylating agent in the presence of an acid binding agent in an aqueous-organic solvent or diluent in a pH range from 8 to 14 at a temperature from 20° to 150° C.; and E. deacetylating the product of step D by contacting the same at reflux with an aqueous alkali metal hydroxide.

* * * * *